(12) United States Patent
He et al.

(10) Patent No.: US 9,980,918 B2
(45) Date of Patent: May 29, 2018

(54) ACID RESISTANT BANDING SOLUTION FOR ACID RESISTANT TWO PIECE HARD CAPSULES

(71) Applicant: Capsugel Belgium NV, Bornem (BE)

(72) Inventors: Xiongwei He, Andolsheim (FR); Dominique Nicolas Cade, Colmar (FR)

(73) Assignee: Capsugel Belgium NV, Bornem (BE)

( * ) Notice: Subject to any disclaimer, the term of this patent is extended or adjusted under 35 U.S.C. 154(b) by 0 days. days.

(21) Appl. No.: 15/332,915

(22) Filed: Oct. 24, 2016

(65) Prior Publication Data

US 2017/0035699 A1 Feb. 9, 2017

Related U.S. Application Data

(63) Continuation of application No. 14/357,202, filed as application No. PCT/IB2012/003133 on Nov. 8, 2012.

(60) Provisional application No. 61/557,623, filed on Nov. 9, 2011, provisional application No. 61/577,127, filed on Dec. 19, 2011.

(51) Int. Cl.
*A61K 9/48* (2006.01)
*A23P 10/30* (2016.01)
*A61K 31/167* (2006.01)

(52) U.S. Cl.
CPC ............ *A61K 9/4883* (2013.01); *A23P 10/30* (2016.08); *A61K 9/4808* (2013.01); *A61K 9/4816* (2013.01); *A61K 9/4891* (2013.01); *A61K 31/167* (2013.01); *A23V 2002/00* (2013.01)

(58) Field of Classification Search
None
See application file for complete search history.

(56) References Cited

U.S. PATENT DOCUMENTS

| 2,924,920 | A | 2/1960 | Margolis |
| 3,071,513 | A | 1/1963 | De Boer |
| 3,927,195 | A | 12/1975 | Messora |
| 4,138,013 | A | 2/1979 | Okajima |
| 4,734,149 | A | 3/1988 | Brown |
| 4,756,902 | A | 7/1988 | Harvey et al. |
| 4,761,932 | A | 8/1988 | Harvey et al. |

(Continued)

FOREIGN PATENT DOCUMENTS

| EP | 0152517 | 8/1985 |
| EP | 0460921 | * 11/1991 |

(Continued)

OTHER PUBLICATIONS

Notice of Reasons for Rejection issued by Japan Patent Office for Japanese Application No. 2014-540574 dated Dec. 20, 2016, 13 pages (with English translation).

(Continued)

*Primary Examiner* — Melvin C Mayes
*Assistant Examiner* — Colette Nguyen
(74) *Attorney, Agent, or Firm* — Klarquist Sparkman, LLP

(57) ABSTRACT

The present disclosure relates to acid resistant banding solutions for two piece hard capsules endowed with acid resistant properties, and methods of making and using acid resistant banding solutions. The present disclosure also relates, in part, to methods for banding such acid resistant capsules which provides an acid resistant seal between the capsule parts and achieves increased acid resistance in vitro.

14 Claims, 1 Drawing Sheet

(56) References Cited

U.S. PATENT DOCUMENTS

| | | | |
|---|---|---|---|
| 4,816,259 A | | 3/1989 | Matthews et al. |
| 4,922,682 A | | 5/1990 | Tait et al. |
| 4,940,499 A | | 7/1990 | Lebrun et al. |
| 5,054,208 A | | 10/1991 | Gillette et al. |
| 5,283,064 A | * | 2/1994 | Suzuki ............... A61K 9/4816 424/436 |
| 7,094,425 B2 | | 8/2006 | Scott et al. |
| 7,229,639 B2 | | 6/2007 | Guillard et al. |
| 8,181,425 B2 | | 5/2012 | McCutcheon et al. |
| 2003/0194431 A1 | * | 10/2003 | Miller ............... A61J 3/071 424/451 |
| 2004/0028737 A1 | * | 2/2004 | Deshpande ......... A61K 9/2846 424/474 |
| 2004/0170688 A1 | | 9/2004 | Deshmukh et al. |
| 2007/0065501 A1 | | 3/2007 | He et al. |
| 2010/0212261 A1 | * | 8/2010 | Boldis ............... A61J 3/071 53/403 |
| 2011/0033530 A1 | * | 2/2011 | Skalsky ............... A23P 1/04 424/456 |
| 2012/0244219 A1 | | 9/2012 | Lahav et al. |
| 2015/0140084 A1 | | 5/2015 | Takubo |

FOREIGN PATENT DOCUMENTS

| | | |
|---|---|---|
| FR | 2118883 | 8/1972 |
| GB | 759274 | 10/1956 |
| JP | S5732230 | 2/1982 |
| JP | S63117761 | 5/1988 |
| JP | H08 245423 | 9/1996 |
| JP | H0987169 | 3/1997 |
| JP | 2006016372 | 1/2006 |
| JP | 2010202550 | 9/2010 |
| WO | WO 98/18454 | 5/1998 |
| WO | WO 2005/026233 | 3/2005 |
| WO | WO 2006070578 | 7/2006 |
| WO | WO 2007/020529 | 2/2007 |
| WO | WO 2011/002972 | 1/2011 |
| WO | WO 2011/036601 | 3/2011 |

OTHER PUBLICATIONS

International Search Report and Written Opinion issued for International Application No. PCT/IB2012/003133, dated Apr. 9, 2013, 8 pages.
Notice of Reasons for Rejection for corresponding Japanese Patent Application No. 2014-540574, dated Jul. 12, 2016, 7 pages (with English-language translation).
International Search Report and Written Opinion issued for International Application No. PCT/EP2016/068834, dated Sep. 16, 2016, 12 pages.
"Shellac," Wikipedia, https://en.wikipedia.org/wiki/Shellac (retrieved Oct. 24, 2016), 6 pages.

* cited by examiner

ACID RESISTANT BANDING SOLUTION FOR ACID RESISTANT TWO PIECE HARD CAPSULES

This application is a continuation of U.S. patent application Ser. No. 14/357,202, filed May 8, 2014, now abandoned, which is a national stage entry under 35 U.S.C. § 371 of International Application No. PCT/IB2012/003133, filed Nov. 8, 2012, which claims the benefit of and priority to U.S. Provisional Applications Nos. 61/557,623, filed Nov. 9, 2011, and 61/577,127, filed Dec. 19, 2011, all of which are incorporated herein by reference in their entirety.

The present disclosure relates to acid resistant banding solutions for banding acid resistant two piece hard capsules, and use of such capsules for example for oral administration of at least one of pharmaceuticals, veterinary products, foods and dietary supplements to humans or animals.

Two piece hard capsules are the oral dosage form preferred by patients, and have traditionally been made from gelatin for more than a century. Over the past twenty years, new types of hard capsules have been developed with alternative raw materials, mainly with hypromellose and pullulan. All these capsules are of immediate release or designed for releasing their content in the stomach rapidly after administration.

Efforts were made to impart a specific functionality to the hard capsules. The most successful example is the gastric resistant hard capsules which can protect the content from the acid conditions, with a delayed release or an intestinal release. Generally, such capsules are utilized in the pharmaceutical and food industries to hold pharmaceutically active materials such as medicines, vitamin preparations and other edibles both solid and liquid and protect them from the acid conditions in the stomach.

Delayed release capsules resistant to the acid conditions of the stomach were developed early on using gelatin insolubilization by treatment with formaldehyde. See, e.g., Ridgway et al., *Hard Capsule Development & Technology*, The Pharmaceutical Press, 1978, p. 11.

With the development of capsule coating technology the enteric hard capsules ("enteric coated capsules") became more popular on the pharmaceutical market. See, e.g., Ridgway et al., *Hard Capsule Development & Technology*, The Pharmaceutical Press, 1978, pp. 229 to 232.

In both above cases, the capsule itself is of immediate release, and its acid resistance is achieved by a post-manufacturing treatment of the capsule, generally after the filling of the capsule in the pharmaceutical company site.

More recently, an intrinsically acid resistant HPMC hard capsule was developed and marketed under the name of DRCAPS™ capsules by CAPSUGEL®. This capsule is made with an acid resistant HPMC formula. Consequently, the capsule shell itself is acid resistant and does not need a post-fill treatment to attain acid resistance.

Further evaluation of DRCAPS™ capsules has revealed that there remains a risk under some conditions for the two parts of the capsule, body and cap, to become separated; for example, under the mechanical stress of in vitro dissolution testing, notably during the in vitro disintegration test under acid conditions. Similarly, diffusion of dissolution medium into the closed capsule and/or diffusion of content from the capsule through the gap between body and cap remain a risk.

Consequently, there is a need to develop a way to effectively prevent the body-cap separation and the diffusion through the gap during the in vitro dissolution tests, and thus to improve the in vivo acid resistance performance of the final dosage form.

A number of solutions to decrease the leakage through the body-cap gap have been developed. For example, hard gelatin capsule banding with a gelatin banding solution is commonly used to prevent the content leakage during storage.

Another method to decrease leakage is to seal the cap and the body of the capsule directly to each other by means of a "sealing fluid." See, e.g., U.S. Pat. No. 3,071,513; U.S. Pat. No. 2,924,920; FR 2,118,883, EP 0152517; U.S. Pat. No. 4,756,902; FR 2 118883; EP 0152517; and U.S. Pat. No. 4,756,902. Methods of banding two piece hard capsules, as well as apparatuses for banding are disclosed, for example, in U.S. Pat. Nos. 8,181,425; 7,229,639; 7,094,425; 5,054,208; 4,940,499; 4,922,682; 4,761,932 and 4,734,149, all of which are incorporated by reference herein.

Furthermore, the development of acid resistant capsules, and hypromellose capsules such as, for example, hydroxypropylmethylcellulose (HPMC) DRCAPS™ (CAPSUGEL®) capsules, created a need to adapt the composition of the banding solution to the polymer properties in order to assure acid resistance of the banded capsule. See, e.g., WO2007/020529; WO2011/036601.

All the previously known ways of banding did not exhibit appropriate acid resistance, and therefore dissolved in acid media during in vitro testing, and also in the acid conditions of the stomach. Thus, there existed a need to develop a safe and effective method for use in acid resistant capsules to prevent body-cap separation and the diffusion through the gap.

DEFINITIONS

As used herein, the following words, phrases, and symbols are generally intended to have the meanings as set forth below, except to the extent that the context in which they are used indicates otherwise.

The terms "optional" or "optionally" means that the subsequently described event, component, or circumstance may or may not occur, and that the description includes instances where the event, component, or circumstance occurs, and instances in which it does not.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise indicated, "cellulose acetate phthalate" is also referred to as CAP, and is commonly known in the field of polymers with the following alternative nomenclature: cas registry number 9004-38-0; chemical common synonyms, such as: acetyl phthalyl cellulose, cellulose acetate hydrogen 1,2-benzenedicarboxylate, cellulose acetate hydrogen phthalate, cellulose acetate monophthalate, cellulose acetophthalate, and cellulose acetyl phthalate; and non proprietary names, such as: cellacephate (British Pharmacopeia), cellulose acetate phthalate (Japanese Pharmacopeia), cellulosi acetas phthalas (PhEur), and cellacefate (U.S. Pharmacopeia).

Unless otherwise indicated, "cellulose acetate trimellitate" is also referred to as CAT.

Unless otherwise indicated, "hydroxypropylmethylcellulose acetate succinate" is also referred to as HPMCAS.

Unless otherwise indicated, "hydroxypropyl methylcellulose phthalate" is also referred to as HPMCP.

Unless otherwise indicated, "carboxy methyl ethyl cellulose" is also referred to as CMEC.

Unless otherwise indicated, "polyvinyl derivatives" includes but is not limited to polyvinyl acetate phthalate which is also referred to as PVAP.

Unless otherwise indicated, the term "room temperature" means about 18° C. to about 28° C., and more particularly from about 20° C. to about 24° C. (22° C.+/−2° C.).

Unless otherwise indicated, the term "acid resistant two piece hard capsules" refers to two piece hard capsules described as acid resistant, or manufactured from acid resistant formulas or obtained by appropriate treatment post the capsule manufacturing, and includes but is not limited to capsules as described in WO 2011/030952, EP22236851, and/or U.S. 2010/113620 A1.

BRIEF DESCRIPTION OF THE DRAWINGS

The accompanying drawings, which are incorporated in and constitute a part of the specification, illustrate presently embodiments of the present disclosure, and together with the general description given above and the detailed description of the embodiments given below, serve to explain the principles of the present disclosure.

DETAILED DESCRIPTION

Figure 1:
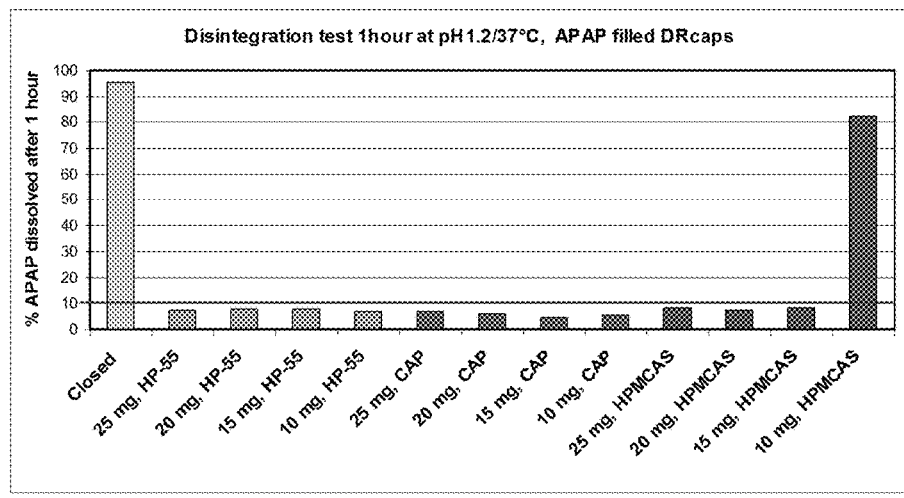
FIG. 1 is a disintegration test at pH 1.2.

Accordingly, one aspect of the present disclosure provides acid resistant banding solutions for banding acid resistant two piece hard capsules, wherein said capsules comprise telescopically engaged capsule parts and are endowed with improved acid resistance properties compared to such capsules closed but without banding.

In another aspect, the present disclosure provides an acid-resistant banding composition comprising an acid resistant polymer, at least one neutralizing compound such as an alkaline compound, and water as solvent.

In another aspect, the present disclosure provides a method for banding two piece capsules which provides an acid resistant seal between the capsule parts and achieves an increased acid resistance in vitro.

In a further aspect, the present disclosure relates to banding solutions for acid resistant capsules, and methods of banding acid resistant capsules with an acid resistant banding solution, which can be achieved without the use of organic solvents, and taking advantage of conventional banding techniques and equipment. See, e.g., F. Podczeck and B. Jones, *Pharmaceutical Capsules*, 2$^{nd}$ Ed., Pharmaceutical Press (2004), pp. 182-183.

In one embodiment, a banding composition and method for banding acid resistant hard capsules is provided comprising at least one acid resistant polymer, at least one alkaline compound, and water.

In another embodiment, the at least one acid resistant polymer in the banding composition for hard capsules is selected from the group consisting of methacrylic acid copolymers (copolymers of methacrylic acid and either methyl methacrylate or ethyl acrylate such as poly(methacrylic acid-co-ethyl acrylate) 1:1); cellulose acetate phthalate (CAP); cellulose acetate trimellitate (CAT); hydroxypropyl methylcellulose acetate succinate (HPMCAS); hydroxypropyl methylcellulose phthalate (HPMCP); carboxy methyl ethyl cellulose (CMEC); polyvinyl derivatives (e.g., polyvinyl acetate phthalate), and mixtures thereof.

In another embodiment, the at least one alkaline compound of the banding composition is at least one compound selected from the group consisting of sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, and mixtures thereof.

In one embodiment, the acid resistant banding composition is applied to, and therefore further comprises, an acid resistant capsule, and in another embodiment, the acid resistant banding composition is applied to and therefore further comprises a dip molded or injection molded hydroxypropylmethylcellulose (HPMC) acid resistant capsule. In other embodiments, the acid resistant banding composition is applied to, and therefore comprises, an enteric capsule such as a dip molded HPMCAS or CAP capsule.

In one embodiment, the banding composition optionally further comprises at least one pharmaceutically acceptable or food acceptable plasticizer.

In a further embodiment, the banding composition according to the present disclosure may further comprise at least one pharmaceutically acceptable or food acceptable coloring agent.

The present disclosure also provides a method for the preparation of an acid resistant banding solution comprising: dispersing at least one acid resistant polymer in water under mixing; and adding at least one alkaline compound progressively under gentle stirring until the at least one acid resistant polymer is dissolved.

In another embodiment, the method according to the present disclosure provides for the preparation of the banding solution carried out at room temperature. In another embodiment, the method according to the present disclosure provides for the use of the banding solution by banding hard capsules carried out at room temperature. Banding methods include automated and hand applied banding methods. See, e.g., *Capsule Filling* by D. K. Lightfoot, Tablets and Capsules Magazine, CSC Publishing (January 2007).

In a further embodiment, the method for the preparation of an acid resistant banding solution further comprises adjusting the viscosity to a level appropriate for the hard capsule banding method. Non-limiting examples of appropriate viscosity for an acid resistant hard capsule banding solution and method are, for example, viscosities from about 50 cP to about 10,000 cP at room temperature; from about 100 cP to about 5000 cP; and from about 1500 cP to about 3100 cP. Desired viscosity is obtained by adjusting the concentration of the solution (i.e., by varying the amount of water and/or the amount of polymer).

In other embodiments, the method for the preparation of an acid resistant banding solution further comprises adding to the solution at least one pharmaceutically acceptable or food acceptable plasticizer and/or at least one pharmaceutically acceptable or food acceptable coloring agent.

Examples of pharmaceutically acceptable or food acceptable coloring agents include but are not limited to soluble dyes, including Tartrazine E102, FD&C Yellow 5D&C Yellow 10; Sunset Yellow E110, FD&C Yellow 6; D&C Red No. 22; D&C Red No. 28; D&C Red No. 33 (Acid Fushine); Allura Red E129, FD&C Red 40; Indigo carmine E132, FD&C Blue 2; Brilliant Blue FCF E133, FD&C Blue 1;

Caramel, USP E150c; FD&C Green 3; FD&C red 3/Erythrosine; Azorubine; Brilliant Black; Chlorophyllin Copper Complex or sodium copper chlorophyllin; Ponceau 4R; Patent Blue V; Quinolone yellow; Curcumin, Red cabbage; and mixtures thereof. Other examples of pharmaceutically acceptable or food acceptable coloring agents include but are not limited to pigments, including Titanium Dioxide, Yellow Iron Oxide, Red Iron Oxide, Black Iron Oxide, Candurin silver fine, and mixtures thereof.

The present disclosure also provides a method for banding an acid resistant hard capsule as described herein with an acid resistant banding composition comprising at least one acid resistant polymer, at least one alkaline compound, and water. The method includes determining the desired banding composition amount, measuring the banding composition required, and applying the banding composition to the acid resistant capsule.

The present disclosure also provides an effective acid resistant banding of acid resistant hard capsules even with low band thickness or weight, such as lower than 10 mg, or even lower than 5 mg. These values are calculated based on the quantity, deposit, and concentration of the banding solution and results obtained for the dry band weight for size 0 capsules, and will be proportional for smaller capsules. The band weight is adapted as a function of the capsule size.

The following non-limiting examples are offered to clarify the disclosure and are not intended to limit the scope of the present claims. The acid resistant capsules used in the banding examples are DRcaps™ capsules (HPMC) of size 0, natural transparent (N.T.) from CAPSUGEL®, but any acid resistant capsule may be used. The banding solutions and methods according to the present disclosure can be applied to any size of DRcaps™ capsules or to any size of other acid resistant two piece capsules. The banding solution of the present disclosure can be applied to any two piece hard capsules with acid resistance performance, for example but without limitation, enteric capsules fabricated from hydroxypropylmethylcellulose acetate succinate (HPMCAS) or from cellulose acetate phthlalate CAP) may be banded using the banding solutions and methods according to the present disclosure.

EXAMPLES

Three samples of banding solution were prepared using the HPMCP (HP-55), CAP, or HPMCAS respectively as acid resistant polymers. The alkaline compound used was an aqueous ammonia solution with a 35% $NH_3$ concentration (ammonia solution 0.88 S.G. (35% $NH_3$) from Fisher Scientific). The appropriate quantity by weight of polymer powder was first dispersed in the water at room temperature under stirring to obtain the desired weight ratio (see Table 1). Then the indicated amount of ammonia solution was added to the dispersion progressively under gentle stirring until the polymer particles were totally dissolved. A 0.1% solution of Patent Blue V-C.I. Food Blue 5 E131 (based on the polymer weight) was added to aid in the visualization of the banding. Table 1 presents the compositions and characteristics of the obtained banding solutions.

TABLE 1

| Chemical name | Supplier | Grade | Quantity (g) | Water (g) | Concentration (%, w/w) | $NH_3$ (35%) (ml) | Viscosity (cPs) at 22° C. | pH |
|---|---|---|---|---|---|---|---|---|
| HPMCP | Shin-Etsu | HP-55 | 100 | 400 | 20.0 | 17.5 | 1570 | 4.9 |
| CAP | Eastman | CAP, NF | 82.5 | 417.5 | 16.5 | 19.8 | 1959 | 7.4 |
| HPMCAS | Shin-Etsu | Aquot AS-LG | 85 | 415 | 17.0 | 6.7 | 3012 | 5.5 |

DRcaps™ capsules, size 0 were used for these banding tests. Capsules were first filled with a blend of lactose and FD&C Blue 2 or Acetyl paraminophenol (APAP) for visual disintegration testing or dissolution dosage testing, respectively.

The band thickness or amount needed to provide an effective acid resistant banding was determined by the screening of the banding solution quantity applied on the capsule. The quantity of the banding solution applied on the capsules was determined by weighing the capsule before and immediately after the banding procedure and comparing the weights obtained. Banding was performed on a lab scale banding equipment from MG2 (Model SUM) with drying under room temperature conditions.

The banded capsules were tested using the United States Pharmacopeia ("USP") disintegration method (Chapter 701) in pH 1.2 media and evaluated by the visual approach. Accordingly, the sample capsules were filled with a blend of lactose and FD&C Blue 2. Table 2 summarizes the visual results of the test for the size 0 capsules.

TABLE 2

| | | Disintegration with disc at pH 1.2 USP/37° C. Sample size n = 6 capsules | | | | | |
|---|---|---|---|---|---|---|---|
| | Approx. banding solution weight (mg) | State at 30 min | | | State at 1 hour | | |
| Banding Polymer | | # Leaked | # Emptied | # Shell disintegration | # Leaked | # Emptied | # Shell disintegration |
| HP-55 | 25 | 0 | 0 | 0 | 0 | 0 | 0 |
| | 20 | 0 | 0 | 0 | 0 | 0 | 0 |
| | 15 | 0 | 0 | 0 | 1 | 0 | 0 |
| | 10 | 0 | 0 | 0 | 1 | 0 | 0 |

TABLE 2-continued

Disintegration with disc at pH 1.2 USP/37° C.
Sample size n = 6 capsules

| Banding Polymer | Approx. banding solution weight (mg) | State at 30 min | | | State at 1 hour | | |
|---|---|---|---|---|---|---|---|
| | | # Leaked | # Emptied | # Shell disintegration | # Leaked | # Emptied | # Shell disintegration |
| CAP | 25 | 0 | 0 | 0 | 0 | 0 | 0 |
| | 20 | 0 | 0 | 0 | 0 | 0 | 0 |
| | 15 | 0 | 0 | 0 | 0 | 0 | 0 |
| | 10 | 0 | 0 | 0 | 0 | 0 | 0 |
| HPMCAS | 25 | 0 | 0 | 0 | 0 | 0 | 0 |
| | 20 | 0 | 0 | 0 | 0 | 0 | 0 |
| | 15 | 0 | 0 | 0 | 0 | 0 | 0 |
| | 10 | 0 | 0 | 0 | 4 | 1 | 0 |

The HP-55 banding solution was effective at about 20 mg or greater banding solution weight for size 0 capsules. The CAP banding solution was effective at all weights tested for size 0 capsules, i.e., about 10 mg or greater banding solution weight. The HPMCAS polymer banding solution was effective at about 15 mg or greater banding solution weight. Because the banding solution weight is proportional to the capsule size (i.e., diameter), these results for size 0 capsules (with a diameter of about 0.3 inches) may be extrapolated to smaller capsules, since smaller capsules would require less banding solution by weight.

The banded capsules filled with APAP were tested using the USP disintegration method in pH 1.2 media and evaluated by the dosage approach, which measures the % of APAP dissolved after an hour disintegration test at pH 1.2. Table 3 and FIG. 1 summarize the results of the test.

TABLE 3

| DRCAPS™ Capsules, #0 | 1 hour disintegration test at pH 1.2/37° C. USP | | | | | | | | |
|---|---|---|---|---|---|---|---|---|---|
| Banding type | Closed | | HP-55 banding | | | | | | |
| Banding quantity | 0 | | 25 mg | | 20 mg | | 15 mg | | 10 mg |
| Tested N Observation | N = 3 Opened | N = 3 Opened | N = 3 | N = 3 Resistant | N = 3 | N = 3 | N = 3 | N = 3 | N = 3 N = 3 4/6 cap moved |
| % APAP dissolved | 97.7 | 92.6 | 6.2 | 8.4 | 8.0 | 7.4 | 8.4 | 6.9 | 6.3  7.7 |
| AVG % APAP Dissolved | 95.2 | | 7.3 | | 7.7 | | 7.7 | | 7.0 |
| Banding type | | | CAP banding | | | | | | |
| Banding quantity | | | 25 mg | | 20 mg | | 15 mg | | 10 mg |
| Tested N Observation | / | | N = 3 | N = 3 Resistant | N = 3 | N = 3 | N = 3 | N = 3 | N = 3  N = 3 |
| % APAP dissolved | | | 6.7 | 6.7 | 5.8 | 5.7 | 4.4 | 4.5 | 6.7  4.1 |
| AVG % APAP Dissolved | | | 6.7 | | 5.8 | | 4.5 | | 5.4 |
| Banding type | | | HPMCAS banding | | | | | | |
| Banding quantity | | | 25 mg | | 20 mg | | 15 mg | | 10 mg |
| Tested N Observation | / | | N = 3 | N = 3 Resistant | N = 3 | N = 3 | N = 3 | N = 3 | N = 3  N = 3 5/6 opened 1/6 cap moved |
| % APAP dissolved | | | 8.6 | 8.5 | 7.2 | 7.5 | 8.8 | 7.6 | 94.0  70.5 |
| AVG % APAP Dissolved | | | 8.5 | | 7.4 | | 8.2 | | 82.3 |

Figure 2:
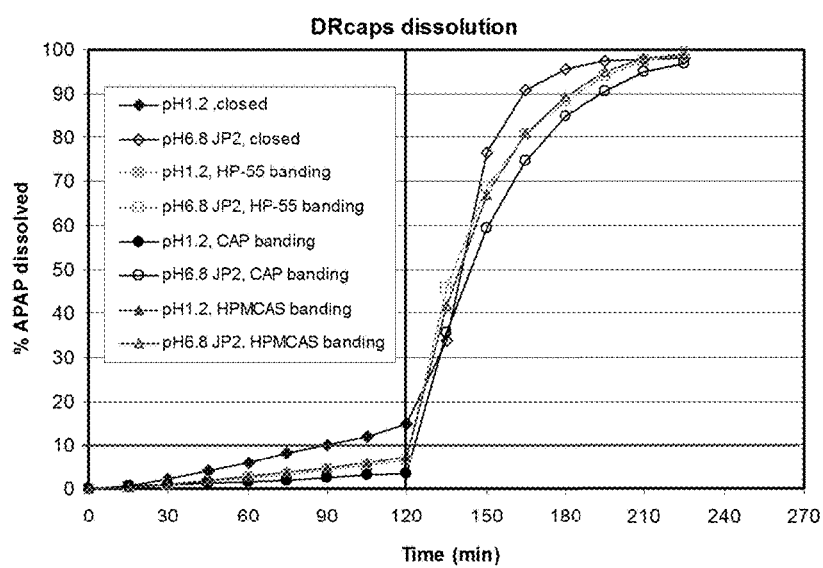
FIG. 2 is a dissolution test as a function of time.

Table 4 and FIG. 2 present the results obtained with the banded capsules filled with APAP by the dosage method assay (the APAP (acetaminophen) concentration in the dissolution media was measured with a UV spectrophotometer at a wavelength of 300 nm and compared to known concentration standards) in order to determine the % of APAP dissolved over a period of up to 240 minutes by the USP dissolution test (Chapter 711) and the Japanese Pharmacopoeia dissolution test (Chapter 9.41) methods. Six capsules were tested for each data point.

TABLE 4

| Medium | DRCAPS ™ Capsules, #0 Time (min) | Closed | Banded with HP-55 | Banded with CAP | Banded with HPMCAS |
|---|---|---|---|---|---|
| | | | % APAP dissolved | | |
| pH1.2/37° C. USP | 0 | 0.0 | 0.0 | 0.0 | 0.0 |
| | 15 | 0.7 | 0.4 | 0.7 | 0.4 |
| | 30 | 2.1 | 0.9 | 1.0 | 1.1 |
| | 45 | 4.1 | 1.5 | 1.2 | 1.8 |
| | 60 | 6.1 | 2.4 | 1.6 | 2.7 |
| | 75 | 8.1 | 3.3 | 2.0 | 3.8 |
| | 90 | 10.0 | 4.3 | 2.5 | 4.8 |
| | 105 | 12.1 | 5.5 | 3.0 | 5.9 |
| | 120 | 14.8 (max: 18.2) | 6.7 (max: 8.1) | 3.4 (max: 8.1) | 7.1 (max: 8.1) |
| pH6.8/37° C. JP2 | 135 | 33.7 | 45.8 | 35.7 | 41.7 |
| | 150 | 76.5 | 68.7 | 59.4 | 67.0 |
| | 165 | 90.7 (min: 86.0) | 80.7 (min: 72.5) | 74.7 (min: 72.1) | 81.1 (min: 72.8) |
| | 180 | 95.7 | 88.2 | 85.0 | 89.3 |
| | 195 | 97.4 | 94.1 | 90.4 | 95.1 |
| | 210 | 97.9 | 97.5 | 95.0 | 98.1 |
| | 225 | 98.1 | 99.4 | 97.0 | 98.8 |

All of the banding solutions tested were effective at retaining the acid resistance of a two piece HPMC hard capsule, and capsules with the banding solutions tested had greater acid resistance in in vitro testing compared with closed capsules without banding.

In addition to DRCAP™ capsules, enteric capsules such as those fabricated from HPMCAS or from CAP can also be used with the methods according to the Examples and in banding tests such as the USP disintegration method described herein.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A banded capsule dosage form comprising:
   a) an intrinsically acid resistant, two piece hard capsule comprising a body and a cap;
   b) the body and the cap being telescopically engaged to encapsulate an active agent; and
   c) an acid resistant band around the two piece hard capsule that seals a gap between the body and the cap, the acid resistant band comprising at least one acid resistant polymer selected from hydroxypropyl methylcellulose phthalate (HPMCP), cellulose acetate phthalate (CAP), hydroxypropyl methylcellulose acetate succinate (HPMCAS), and mixtures thereof and wherein the acid resistant band is formed of a composition that is substantially free of an organic solvent;
   wherein the banded capsule dosage form provides improved resistance to acid media relative to a non-banded, closed capsule dosage form, as evaluated using a United States Pharmacopeia ("USP") disintegration method (Chapter 701) in pH 1.2 media.

2. The banded capsule dosage form of claim 1 wherein the two piece hard capsule comprises HPMC, HPMCAS, or CAP.

3. The banded capsule dosage form according to claim 1, wherein the acid resistant band further comprises at least one alkaline compound selected from sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, and mixtures thereof.

4. The banded capsule dosage form according to claim 3 wherein the at least one alkaline compound is ammonia.

5. The banded capsule dosage form according to claim 1, wherein the acid resistant band further comprises at least one pharmaceutically acceptable or food acceptable plasticizer and/or coloring agent.

6. The banded capsule dosage form according to claim 1, wherein the at least one acid resistant polymer is HPMCP.

7. The banded capsule dosage form according to claim 1, wherein the at least one acid resistant polymer is CAP.

8. The banded capsule dosage form according to claim 1, wherein the at least one acid resistant polymer is HPMCAS.

9. The banded capsule dosage form according to claim 8, wherein the at least one acid resistant polymer is HPMCAS.

10. The banded capsule dosage form of claim 1, wherein the active agent is a pharmaceutical agent, a veterinary product, a food, or a dietary supplement.

11. A banded capsule dosage form comprising:
    a) an intrinsically acid resistant, two piece hard HPMC capsule comprising a body and a cap;
    b) the body and the cap being telescopically engaged to encapsulate an active agent; and
    c) an acid resistant band around the two piece hard capsule that seals a gap between the body and the cap, the acid resistant band comprising HPMCAS;
    wherein the banded capsule dosage form provides improved resistance to acid media relative to a non-banded, closed capsule dosage form, as evaluated using a United States Pharmacopeia ("USP") disintegration method (Chapter 701) in pH 1.2 media.

12. The banded capsule dosage form according to claim 11, wherein the acid resistant band further comprises at least one alkaline compound selected from sodium bicarbonate, sodium carbonate, potassium carbonate, potassium bicarbonate, sodium hydroxide, tri sodium phosphate, sodium perborate, potassium hydroxide, lithium hydroxide, lithium carbonate, lithium bicarbonate, ammonium carbonate, ammonium bicarbonate, ammonium hydroxide, ammonia, and mixtures thereof.

13. The banded capsule dosage form according to claim 12, wherein the at least one alkaline compound is ammonia.

14. The banded capsule dosage form according to claim 11, wherein the acid resistant band further comprises at least one pharmaceutically acceptable or food acceptable plasticizer and/or coloring agent.

* * * * *